(12) United States Patent
Kilambi

(10) Patent No.: US 8,212,074 B2
(45) Date of Patent: Jul. 3, 2012

(54) NANO-SCALE UREA PARTICLES AND METHODS OF MAKING AND USING THE PARTICLES

(76) Inventor: Srinivas Kilambi, Marietta, GA (US)

(*) Notice: Subject to any disclaimer, the term of this patent is extended or adjusted under 35 U.S.C. 154(b) by 105 days.

(21) Appl. No.: 12/850,837

(22) Filed: Aug. 5, 2010

(65) Prior Publication Data
US 2011/0094277 A1    Apr. 28, 2011

Related U.S. Application Data

(60) Provisional application No. 61/254,888, filed on Oct. 26, 2009.

(51) Int. Cl.
*A01B 79/00* (2006.01)
*C07C 273/04* (2006.01)

(52) U.S. Cl. .................... 564/67; 71/54; 47/58.1 SC

(58) Field of Classification Search .............. 564/67; 71/54; 47/58.1, 58.1 SC
See application file for complete search history.

(56) References Cited

U.S. PATENT DOCUMENTS

| | | | |
|---|---|---|---|
| 3,561,003 A * | 2/1971 | Lanham et al. | 523/340 |
| 5,114,702 A * | 5/1992 | Pederson et al. | 423/639 |
| 6,977,063 B1 * | 12/2005 | Ramshaw et al. | 422/135 |
| 2004/0005258 A1 * | 1/2004 | Fonash et al. | 422/271 |

* cited by examiner

Primary Examiner — Timothy Vanoy

(57) ABSTRACT

Methods for synthesizing nano-urea particles are described. The methods involve using a spinning cone reactor, a nano-channel reactor, combustion synthesis or spray drying. Ammonia and carbon dioxide are used as raw materials for producing urea. The methods allow for the production of urea nanoparticles at high conversion rates. The methods allow for better control over the hydrolysis rate of the nano-urea particles. The nano-urea particles can be used as fertilizers and provide for sustained release of ammonia and its conversion to nitrates in the soil. The nano-urea particles have low volatilization rates, low moisture absorption rates and low biuret concentration. The nano-urea particles can be applied to the soil via fertigation.

22 Claims, 6 Drawing Sheets

NANO-SCALE UREA PARTICLES AND METHODS OF MAKING AND USING THE PARTICLES

This application claims the benefit of Provisional Application No. 61/254,888, filed Oct. 26, 2009, which is incorporated by reference herein in its entirety.

TECHNICAL FIELD

The invention relates generally to methods for the manufacture of nano-scale urea particles. The methods involve using a spinning cone reactor, a nano-channel reactor, combustion synthesis or spray drying. The methods allow for better control over the hydrolysis rate of the resulting urea particles for sustained release of ammonia and its conversion to nitrates. Other advantages include low volatilization rates, lower moisture absorption rate and lower biuret concentration. The urea particles can be applied through an irrigation system (i.e, via fertigation).

BACKGROUND

Urea, an organic compound, has two amine groups along with a carbonyl functional group. It metabolizes the nitrogen compounds in animals and is the main source of nitrogen in the urine of mammals. Urea is a colorless, odorless solid which is neither acidic nor basic. It is highly soluble in water. It is used as a fertilizer as the source of Nitrogen. The original production of urea was from the reaction between silver isocyanate and ammonium chloride:

$$AgNCO + NH_4Cl \rightarrow (NH_2)_2CO + AgCl.$$

Urea is widely used as a fertilizer and it is believed that more than 80% of the world's urea production is used as a fertilizer. It has the highest nitrogen content (46%) of all solid nitrogen based fertilizers used. Urea in the soil is converted to ammonia by hydrolysis. The ammonia is then oxidized to nitrates by the bacteria present in the soil. The nitrates are the absorbed by the plants for its nutrients. Urea is also used as a base for the manufacture of many other nitrogen based fertilizers.

Commercially, urea granules are used over the regular prills since granules have smaller particle size distribution. This is a major advantage for mechanical application. Nano-granules of urea will have better mechanical application because the particle size is even narrower than the granules and a positive charge can be imparted to the particles to form an ionic bond with most soils which are negatively charged.

Urea decomposes into biuret which is very harmful for plant growth. Biuret is a very common impurity of urea. Biuret formation can occur when urea is subjected to heat above its melting point. The biuret content should be minimized to less than 3 mole percent in urea.

Urea is generally applied to the farms at intervals to minimize leaching losses. Urea loss due to volatilization can be minimized by adding it either during or before rains.

Currently, only 20-30% of N/P/K fertilizers reach the soil and then plant roots and get fixed. This causes the rest of the fertilizers to be washed away and results in eutrophication. This involves high usage of fertilizers and less grain yield. The potential to produce 2-3 times more than is currently possible is lost due to the several reasons explained above.

There exists a need for urea particles with improved properties for fertilizer applications as well as more economical and efficient methods of making urea particles.

SUMMARY

A method is provided which comprises:
introducing ammonia and carbon dioxide into a nano-channel reactor; and
allowing the ammonia and carbon dioxide to react to form urea particles.

A method is also provided which comprises:
introducing ammonia gas and supercritical carbon dioxide gas into a reactor;
allowing the ammonia and carbon dioxide to react to form a urea solution;
pressurizing the urea solution;
passing the pressurized urea solution through a nozzle to form a spray of droplets of the urea solution; and
drying the droplets to form urea particles.

A method is also provided which comprises:
contacting ammonia and carbon dioxide with rotating surfaces of a spinning cone reactor such that the centrifugal forces generated by the rotating surfaces mix the reactants; and
allowing the ammonia and carbon dioxide to react to form urea particles.

Urea nano particles produced by any of the above methods are also provided. The urea nanoparticles may further comprise a positive or negative charge and/or a coating on a surface thereof. The coating may comprise urethane, sulfur, a polymer, a polyacrylamide, chitosan, chitin or combinations thereof.

A method is also provided which comprises contacting a plurality of urea particles as set forth above with soil.

A method is also provided which comprises mixing a plurality of urea particles as set forth above with water to form an aqueous solution and applying the aqueous solution to soil.

DETAILED DESCRIPTION

Figure 1:
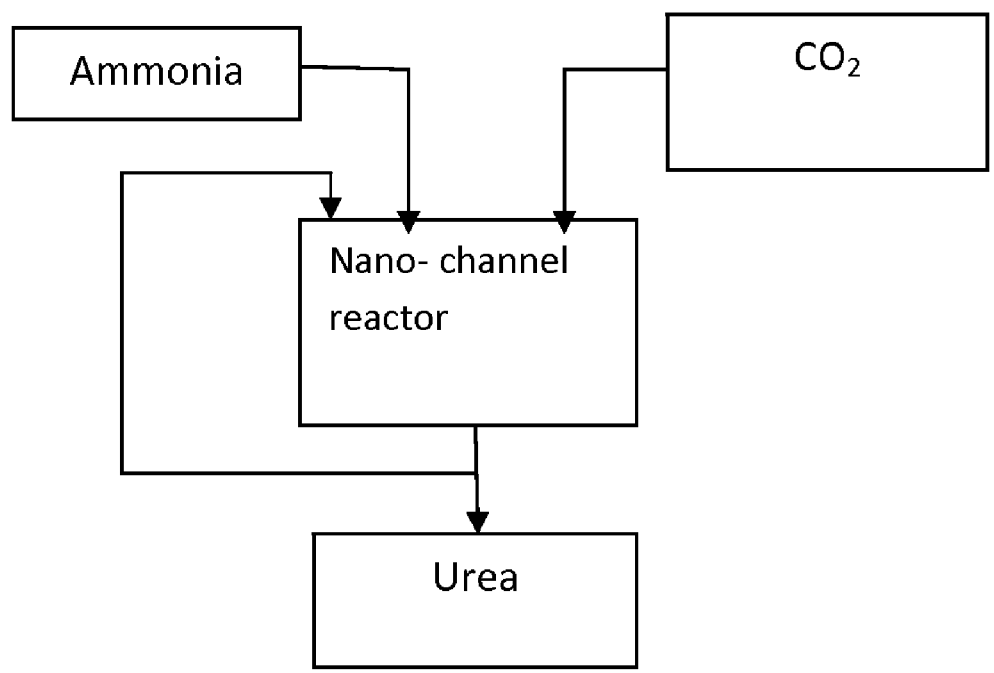
FIG. 1 is a flowchart for the manufacture of nanosized urea using a nano-channel reactor.
Figure 2:
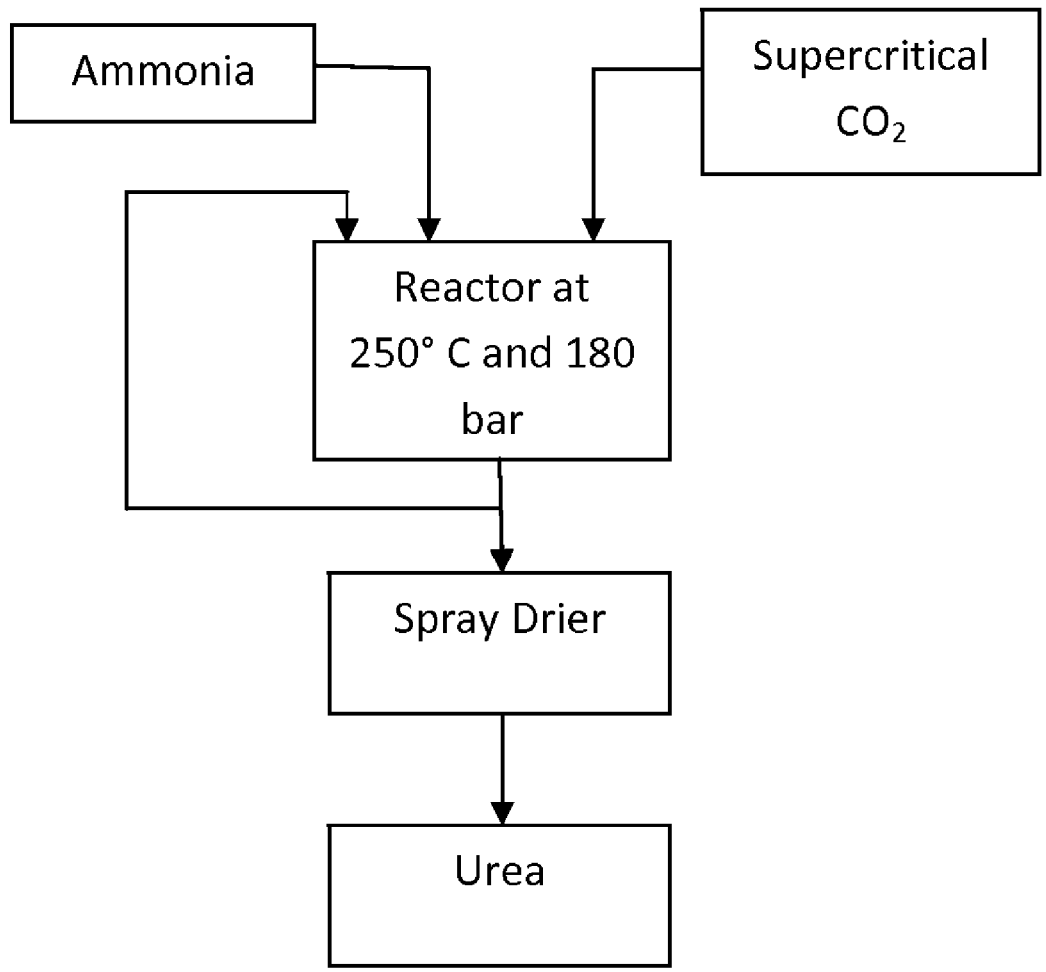
FIG. 2 is a flowchart for the manufacture of nanosized urea using spray drying.
Figure 3:
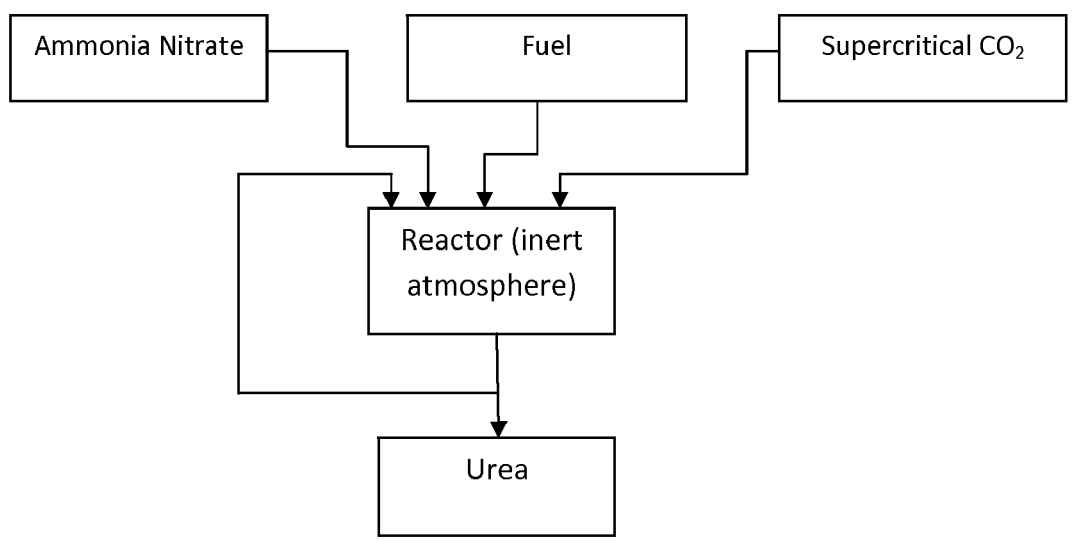
FIG. 3 is a flowchart for the combustion synthesis of nanosized urea.

Disclosed are various methods, apparatus configurations and compositions to produce nanosized urea.

Ammonia and carbon dioxide are conventionally used as reactants in the manufacture of urea. The ammonia and carbon dioxide are fed into a reactor maintained at a temperature of 180-210° C. and a pressure of 180 bar. The two reactions involved in the manufacture of urea are as follows:

$$2NH_3 + CO_2 \leftrightarrow NH_2COONH_4$$

ammonium carbamate $$NH_2COONH_4 \leftrightarrow NH_2CONH_2$$

urea

Both reactions are reversible reactions with the first one being exothermic and the later endothermic. The overall conversion rate of $CO_2$ to urea is usually about 65%.

The urea decomposition to biuret makes it ineligible to be used as a fertilizer. The biuret formation reaction is as follows

biuret

Biuret is the major impurity in urea and it should be eliminated. The current biuret level in urea is about 2%.

This methods described herein allow for an increase in the conversion rate to over 85% and also allow for the production of urea particles with superior properties. The methods described herein can be used to produce a nano-urea which can be easily absorbed in the soil and controlled hydrolysis to ammonia takes place.

A first method involves the use of a spinning cone reactor as a surface for carrying out the synthesis of nanourea. Spinning cone reactors are disclosed in U.S. Pat. No. 6,977,063. This technology uses the rotating surfaces for systems which are heat and mass transfer limited, to achieve good mixing and product yield for viscous reactants. Nanourea can be manufactured using such rotating surfaces for a faster reaction and lower residence times. In this method, the primary reactants (ammonia and carbon dioxide) are reacted on spinning cones which are axially rotated on a common shaft. Centrifugal forces produced by the spinning of the cones cause shearing and formation of thin films leading to process intensification and improvement in heat and mass transfer rates. Additionally this mechanism also facilitates atomization of the nanourea particles and can render surface modification for desired properties in the product.

A second method involves the use of a nano-channel reactor. Nano-channel reactors are know. U.S. Patent Application Publication No. 2004/0005258 A1, for example, discloses chemical nanochannel reactors with micron-scale and nanoscale pores for gas sensing applications. Nano-channel reactors have high density nano-pores in the reaction zone which facilitate faster reaction and higher conversion rates. The nanochannel reactor concept can be used to increase the reactivity of heterogeneous gas mixtures such as ammonia and carbon dioxide to molecular levels in-situ nanochannels, thereby increasing the conversion rates to produce nanourea particles. High density nanochannels can be fabricated with suitable materials to carry-out liquid phase reactions such as the production of nanourea. As described herein, carbon dioxide and ammonia are fed into a nano-channel reactor. For example, the carbon dioxide and ammonia can be fed through nanochannels having pore sizes in the range of 100-500 nm. The two step reaction for the formation of urea can be carried out in-situ the channels. The reactants can be pressurized through the nanochannels to increase reactivity and lower residence times compared to conventional urea processes.

A further method involves the use of the combustion synthesis technique. Combustion synthesis is known. U.S. Pat. No. 5,114,702, for example, discloses a method of preparation of making an aqueous solution of a metal nitrate and an oxidizer by combustion synthesis. As described herein, an ammonia source (e.g. ammonium nitrate), a fuel (e.g. natural gas) and a $CO_2$ source (e.g. dry ice) are used. The ammonia source and $CO_2$ are mixed (e.g., in an inert atmosphere) and heated until the ammonia source (e.g., ammonium nitrate) decomposes. Once the decomposition temperature of the oxidizer is reached, a sudden gush of fuel is released into the reactor. The sudden flow of fuel causes combustion and its propagation with very high reaction temperatures there by forming nanosized urea particles when combustion is complete and on cooling. The fuel used can be natural gas. The combustion synthesis takes place with the reaction products being urea.

An alternate method using a modified combustion synthesis technique can also be efficiently used in deriving more than one product utilizing minimum energy requirements. In this technique, the processes such as combustion of certain metal nitrates to oxides or the nitriding combustion synthesis of metals to their nitrides generates excess amounts of exothermic energy which can be utilized in the production of urea. The excess energy released from the combustion reaction can now be used for two major purposes. Part of the energy is used to decompose an ammonium salt (i.e. ammonium bicarbonate) into ammonia and carbon dioxide as primary raw materials for urea manufacture and a major part in the synthesis reaction to urea. This method is cost effective route to synthesize two products using minimum energy requirements.

A further method involves spray drying. In the spray drying technique, the urea is sprayed through a nozzle into a drying zone and dried to make the nanoparticles of urea. Spray drying method of generating nanoparticles has been used to produce organic and inorganic nanoparticles in an economical fashion. U.S. Pat. No. 3,561,003, for example, discloses particulate inks prepared by using filler in a mixture using spray drying techniques. As described herein, this method involves the use of supercritical fluids such as $CO_2$ along with ammonia gas. The reactants can be in the molar ratio of $CO_2$ to ammonia gas of 1:3. Supercritical carbon dioxide increases the overall conversion of the reaction due to its unique properties. Additionally, spray drying techniques are used to atomize particles of nanosized urea followed by drying techniques.

Several advantages of nano-urea particles as described herein are as follows:
  The particles can have a charge which can either be positive or even negative if desired.
  When positively charged, the particles can form ionic bonds to most soils which are negatively charged resulting in greater nitrogen fixation
  The biuret impurity in nano-urea can be less than 0.3%.
  The particles have low volatilization rates because nano-urea binds with the soil quickly.
  The particles can have controlled hydrolysis rates for better and longer nitrate absorption rate from ammonia thereby reducing the loss
  The particles can be applied via fertigation.
  The particles can have a lower moisture absorption rate.
  The use of nano-urea fertilizers can result in over 100% increase in grain yield.
  The use of nano-urea fertilizers can result in up to a 200% increase in biomass production.

Example 1

Using A Nano-Channel Reactor

Ammonia gas along with supercritical carbon dioxide was passed slowly through a nano-channel reactor. In this type of a reactor, the reaction zone comprises of a series of nanochannels, which can have sieves with nominal diameters of 100-500 nm. Different temperature zones can be maintained along the length of the reactor to carry-out the two step reaction of the manufacture of urea. Higher aspect ratios of these channels will allow higher transfer rates between the reactants leading to increased yields per pass.

The molar ratio of ammonia to carbon dioxide was maintained at 3:1. The temperature and the pressure maintained within the nano-channel reactor were 300° C.-1800° C. and 5-140 bar respectively. Under these conditions the ammonia reacts with supercritical carbon dioxide to form ammonium carbamate as an intermediate and is further concentrated to form urea. The residence time for the reaction is typically in the order of seconds. The overall conversion is over 80%.

The high surface area to volume ratio of these nanochannels enable greater molecular interactions of the reactants by increased mass and heat transfer. Additionally supercritical carbon dioxide in its supercritical condition has almost no surface tension coupled with other properties such as higher diffusivity, lower viscosity than liquids rapidly penetrates the pores of such nanoporous media in the nanochannel reactor allowing a faster reaction rate and increased conversion.

The particle sizes were varied by changing the experimental conditions such as:

Feed to the reactor (change in the molar ratio of reactants for higher conversion);

Temperature and pressure (to reduce the cost of production); and

Residence time (reaction rate).

Example 2

Using Spray Drying

Ammonia gas and supercritical carbon dioxide were passed into the reactor which was maintained at a temperature of 1000° C.-1800° C. and pressure of about 120-140 bar. Under supercritical condition the carbon dioxide gas reacted at faster rate and thereby increasing the conversion rate. The urea solution was then pressurized and passed through a nozzle of 60 micron size. The resultant splash was then dried to get the spray drying effect in order to produce the nano particles.

Figure 4:
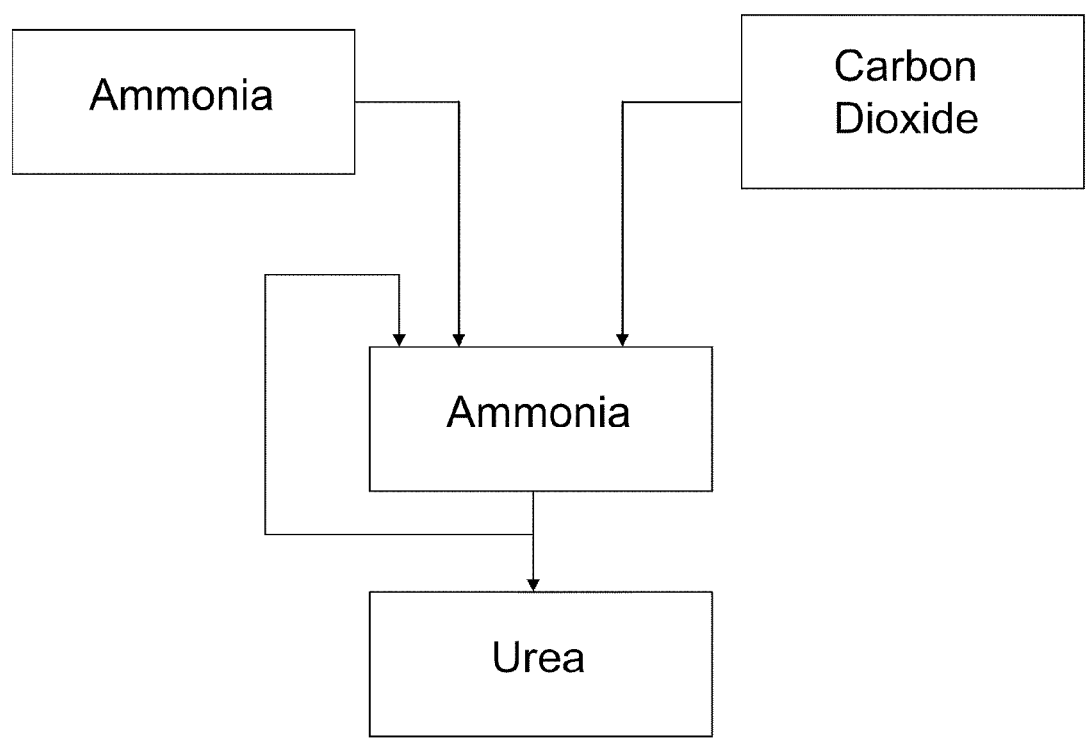
FIG. 4 is a flowchart for the manufacture of nanosized urea using a spinning cone reactor.
Figure 5:
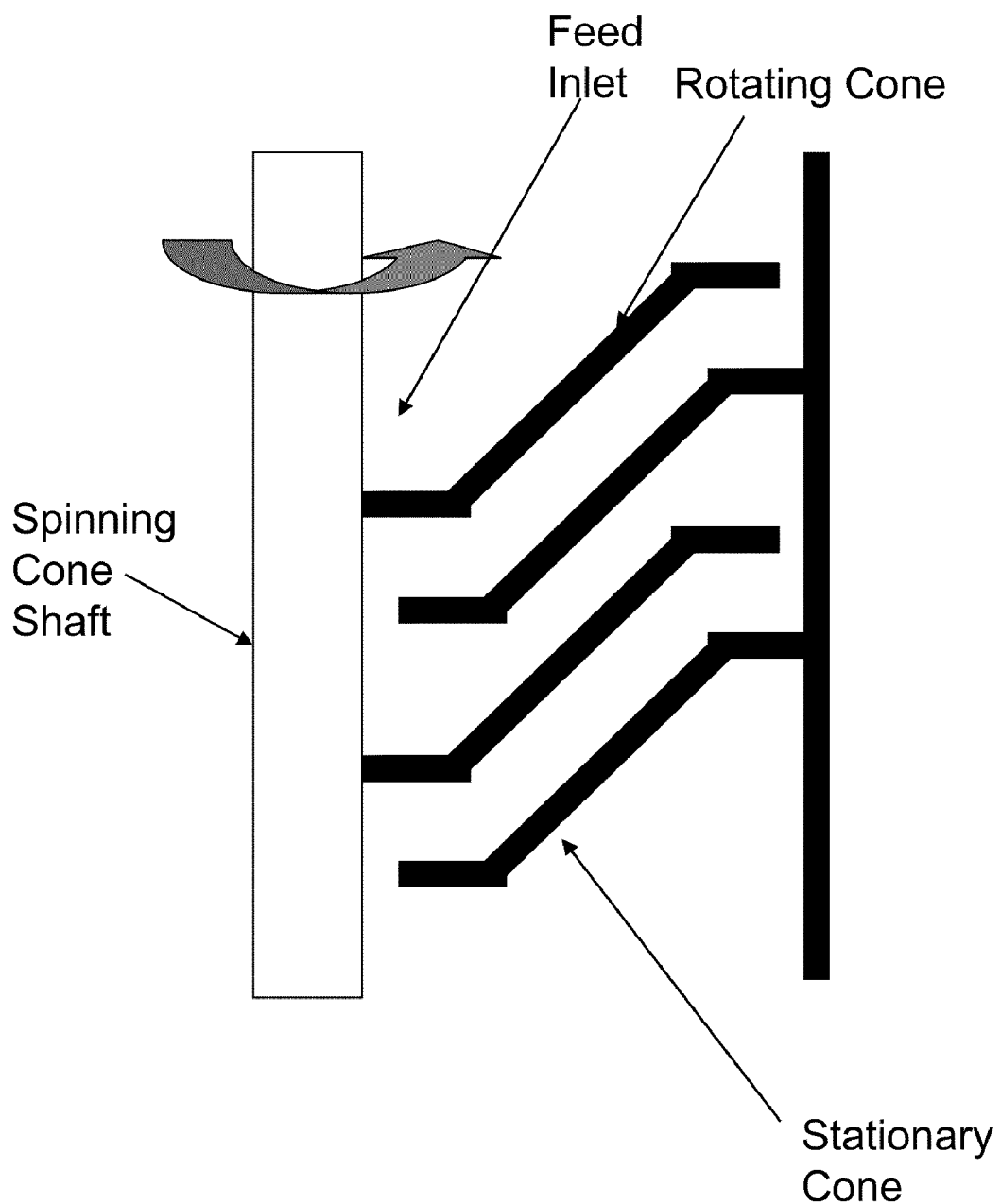
FIG. 5 is schematic of the spinning cone reactor.
Figure 6:
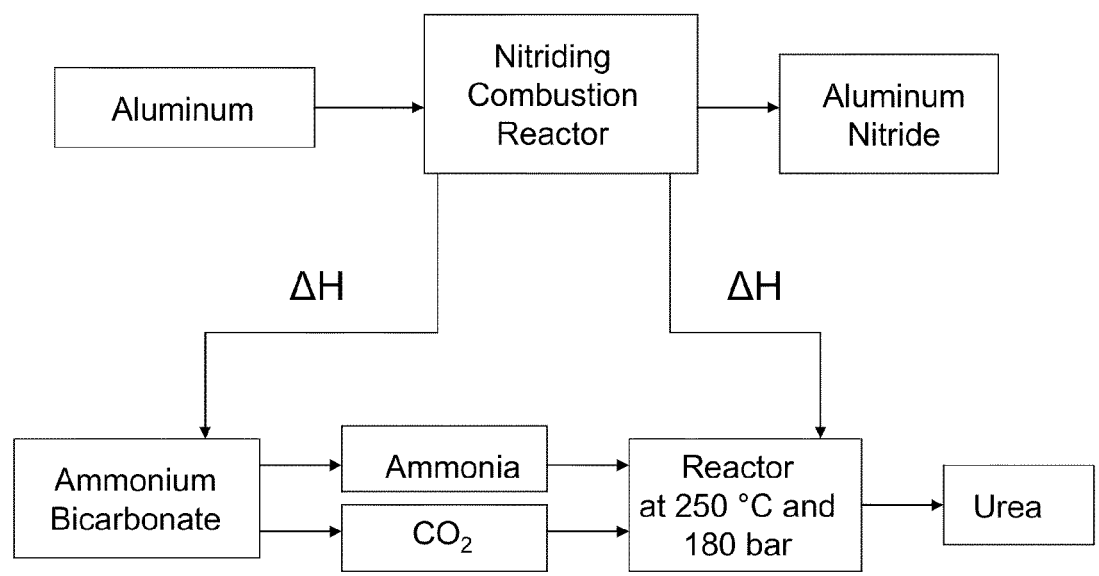
FIG. 6 is a flowchart for the modified combustion synthesis of nanosized urea

The $NH_3$ to $CO_2$ ratio was maintained at 3:1 for better reaction rates of the $CO_2$ and also so that less $CO_2$ would be needed to be recycled. The carbon dioxide sent into the reactor was maintained at supercritical condition of 75 bar pressure and temperature of 320° C. before it entered into the reactor for better efficiency and conversion. FIG. 4 depicts a flow diagram of the above explanation.

Example 3A

Using Combustion Synthesis

Ammonium nitrate along with dry ice is uniformly mixed for homogeneity keeping in mind the ratio of ammonia to carbon dioxide is 3:1. The mixture is then slowly preheated in an inert atmosphere. When the mixture reaches to about 250 degree C., controlled amount of natural gas is passed into the reactor. This creates a sudden burst in temperature and energy. Now the ammonia emitted reacts with the carbon dioxide to form nano urea.

The actual conversion is explained using the reactions below $$NH_4NO_3 \leftrightarrow NH_3 + H_2O + NO_2 + \tfrac{1}{2}O_2$$

ammonia $$2NH_3 + CO_2 \leftrightarrow NH_2COONH_4$$

Ammonium Carbamate $$NH_2COONH_4 \leftrightarrow NH_2CONH_2$$

urea

Different particle sizes were achieved by changing the following conditions:

Experiments were carried out at 75 bar to find out the effect of supercritical $CO_2$.

Experiments were carried out without a fuel due to the exothermic nature of the reaction.

Ammonium nitrate and $CO_2$ at atmospheric pressure and inert atmosphere.

Ammonium nitrate and supercritical $CO_2$ with inert atmosphere.

Ammonium nitrate, supercritical $CO_2$ and fuel at inert atmosphere.

Ammonium nitrate, supercritical $CO_2$ and fuel with continuous air flow in the system.

Example 3B

Using Modified Combustion Synthesis

A modified combustion synthesis can be used to make a metal nitride or oxides, which in-turn generates surplus energy for the synthesis of nanourea as a parallel process. In this multi-step process, the metal oxides or nitrides are synthesized as high value products by combustion synthesis. The excess amount of energy generated by such exothermic reactions of metals to their oxide or nitrides, can be used effectively in the synthesis of urea. In principle, parallel processes can be used to obtain multiple products using minimum energy requirements. As an example, conversion of aluminum to aluminum nitride using nitriding combustion synthesis results in generation of excess exothermic heat which can be used to sustain the low temperature synthesis of nanourea. In the synthesis of nanourea, firstly a source of ammonia and carbon dioxide such as ammonium bicarbonate is decomposed at low temperatures (e.g., 60° C.) to utilize a part of the energy, to derive starting materials for the urea synthesis. Secondly, the energy needed to sustain the conversion of ammonia and carbon dioxide to urea can also be derived from the combustion reaction.

The nitridation (combustion) reaction using nitrogen proceeds as follows:

$$Al + \tfrac{1}{2}N_2 \rightarrow AlN (\Delta H = -318 \text{ kJ/mol}).$$

The exothermic reaction propagates spontaneously and rapidly when the reactant is charged in the powder form in a pressurized nitrogen atmosphere (over 0.5 MPa). The combustion is initiated by using any electrical heater as an ignition source or in a furnace by elevating the temperature momentarily. The nitridition reaction of metal aluminum is typically an exothermic reaction which on initiation goes to completion within seconds. Except the small amount of energy needed to initiate the reaction, no extra energy is needed to carry out the reaction.

Ammonia and carbon dioxide is derived by decomposition of a precursor salt such as ammonium bicarbonate using the surplus heat from the combustion process. Apart from the decomposition reaction the additional energy also sustains the overall urea synthesis process which is carried out at lower temperatures. The decomposition reaction of ammonium bicarbonate decomposes at 36 to 60° C. into ammonia, carbon dioxide and water vapor in an endothermic process.

$$NH_4HCO_3 \rightarrow NH_3 + H_2O + CO_2.$$

Additional ammonia and carbon dioxide for the urea synthesis can be supplied externally in the desired molar ratio of 3:1. The urea synthesis reaction to convert ammonia and carbon dioxide to urea requires temperatures around 200° C. and pressures of 140 bar.

Example 4

Using Spinning Cone Reactors

Spinning cone reactors present a method of process intensification of heat and mass transfer rates, thereby increasing the overall reactivity and reducing residence times. This technology uses the effects of the centrifugal force in generating thin wavy films on the surface of rotating surfaces to induce mixing and shearing between the reactants. Using this technique the ammonia and the carbon dioxide can be contacted as thin films on the surface effectively to have higher reactivity and conversion rates. Alternatively supercritical carbon dioxide can also be used to spread uniformly on the rotating surfaces to achieve homogeneity and higher contact with other reactant.

Internally the Spinning Cone Reactor contains a series of cones. A series of cones that are attached to the rotating shaft are the primary reaction surfaces, whereas a series of parallel cones are attached to the periphery or the wall of the column which act as a series of fixed cones. The fixed cones are attached in such a way that they alternate vertically: one fixed, one rotating, and so on. The reactants are fed from the top of the column on top of one of the cones. Pulled by gravity, the reactant mixture flows down the upper surface of the first fixed cone and drops onto the first rotating cone where, by centrifugal force, the reactant mixture is spun into a thin, turbulent film and forced upward, out and off the rim of the spinning cone, dropping onto the next stationary cone below. In this fashion, the reactants work their way from cone to cone to the bottom of the column.

Example 5

Soil Applications And Corresponding Increase In Yields

A urea nano particle produced according to any of the above described methods is also provided. The nanourea particles can have a positive or negative charge on a surface thereof. The particles can have coatings or be chemically bonded with other molecules. Suitable coatings include urethane, sulfur, polymers, polyacrylamides, chitosan, chitin. The modified particles can provide for sustained or timed release of nitrogen through the modified particle surface.

The urea particles were mixed with water to form an aqueous solution. The aqueous solution and was then applied to soil using an irrigation system.

The aqueous solution when applied to the soil results in slower release of nitrogen and hence better nitrogen fixation by plant roots by 15-100%. This enhanced nitrogen fixation results in 25-100% increase in grains/greens yields/acre and 50-200% increase in biomass yields/acre. This enhanced nitrogen fixation results in lesser runoff of nitrogen to surface and ground water and hence lower eutrophication.

While the foregoing specification teaches the principles of the present invention, with examples provided for the purpose of illustration, it will be appreciated by one skilled in the art from reading this disclosure that various changes in form and detail can be made without departing from the true scope of the invention.

What is claimed is:

1. A method comprising:
   introducing ammonia and carbon dioxide into a nanochannel reactor; and
   allowing the ammonia and carbon dioxide to react to form urea particles.

2. The method of claim 1, wherein the ammonia and carbon dioxide are reacted at a temperature of 30-180° C. and/or wherein the ammonia and carbon dioxide are reacted at a pressure of 5-140 bar.

3. The method of claim 1, wherein the molar ratio of ammonia to carbon dioxide is 2.5:1 to 3.5:1.

4. The method of claim 1, wherein the urea particles have a biuret content of less than 1 mole percent.

5. The method of claim 1, wherein the urea particles have an average diameter of less than 1 µm.

6. A method comprising:
   introducing ammonia gas and supercritical carbon dioxide gas into a reactor;
   allowing the ammonia and carbon dioxide to react to form a urea solution;
   pressurizing the urea solution;
   passing the pressurized urea solution through a nozzle to form a spray of droplets of the urea solution; and
   drying the droplets to form urea particles.

7. A method comprising:
   contacting ammonia and carbon dioxide with rotating surfaces of a spinning cone reactor such that the centrifugal forces generated by the rotating surfaces mix the ammonia and carbon dioxide; and
   allowing the ammonia and carbon dioxide to react to form urea particles.

8. The method of claim 7, wherein the carbon dioxide is supercritical carbon dioxide.

9. The method of claim 7, wherein the ammonia and carbon dioxide are reacted at a temperature of 30-180° C. and/or wherein the ammonia and carbon dioxide are reacted at a pressure of 5-140 bar.

10. The method of claim 7, wherein the molar ratio of ammonia to carbon dioxide is 2.5:1 to 3.5:1.

11. The method of claim 7, wherein the urea particles have a biuret content of less than 1 mole percent.

12. The method of claim 7, wherein the urea particles have an average diameter of less than 1 µm.

13. A urea nano particle produced by the method of claim 1.

14. A urea nano particle produced by the method of claim 6.

15. A urea nano particle produced by the method of claim 7.

16. The urea nano particle of claim 13, further comprising a positive or negative charge or a coating on a surface thereof.

17. The urea nano particle of claim 16, wherein the coating comprises urethane, sulfur, a polymer, a polyacrylamide, chitosan, chitin or combinations thereof.

18. A method comprising:
   contacting a plurality of urea particles as set forth in claim 13 with soil.

19. A method comprising:
   mixing a plurality of urea particles as set forth in claim 13 with water to form an aqueous solution; and
   applying the aqueous solution to soil.

20. The method of claim 19, wherein the aqueous solution is applied to the soil using an irrigation system.

21. The method of claim 3, wherein the molar ratio of ammonia to carbon dioxide is 2.9:1 to 3.1:1.

22. The method of claim 10, wherein the molar ratio of ammonia to carbon dioxide is 2.9:1 to 3.1:1.

* * * * *